(12) United States Patent
Selic

(10) Patent No.: US 8,686,023 B2
(45) Date of Patent: Apr. 1, 2014

(54) SALTS OF SUNITINIB

(75) Inventor: Lovro Selic, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 134 days.

(21) Appl. No.: 13/126,388

(22) PCT Filed: Oct. 28, 2009

(86) PCT No.: PCT/EP2009/064215
§ 371 (c)(1),
(2), (4) Date: Jul. 11, 2011

(87) PCT Pub. No.: WO2010/049449
PCT Pub. Date: May 6, 2010

(65) Prior Publication Data
US 2011/0263671 A1    Oct. 27, 2011

(30) Foreign Application Priority Data
Oct. 28, 2008 (EP) .................................. 08167701

(51) Int. Cl.
*A61K 31/4015* (2006.01)
*C07D 209/10* (2006.01)

(52) U.S. Cl.
USPC .......................................... 514/414; 548/468

(58) Field of Classification Search
USPC ........................................................ 548/468
See application file for complete search history.

(56) References Cited

FOREIGN PATENT DOCUMENTS

| | | |
|---|---|---|
| WO | WO 01/60814 A2 | 8/2001 |
| WO | WO 03/016305 A1 | 2/2003 |
| WO | WO 03/016306 A1 | 2/2003 |
| WO | WO 2009/067686 A2 | 5/2009 |

OTHER PUBLICATIONS

Vippagunta, et al. Advanced Drug Delivery Reviews 48 (2001) 3-26.*
Cancer and Metastasis Reviews (1998),17(1), 91-106.*
Science (1999), vol. 286, 531-537.*
Cancer [online], [retrieved on Jul. 6, 2007] Retrieved from the Internet, URL; http://www nlm nih gov/medlineplus/cancer html>.*
Cancer [online], [retrieved on Jul. 6, 2007]. Retrieved from the Internet, URL; http://en.wikipedia.org/wiki/Cancer>.*
Dong Xioa-Chun et al, Synthesis of Antitumor Agent Sunitinib Malate, Chinese Journal of Medicinal Chemistry, vol. 18, No. 1, pp. 28-31, Feb. 2008.
Harry G. Brittain, Methods for the Characterization of Polymorphs and Solvates,Discovery Laboratories, Inc., Milford, New jersey, 52 pages.
Rajappa Vaidyanathan, 4 The Sutent Story, supplied by the British Library—The World's Knowledge, Printed Jun. 19, 2009, Cited Doc: XP 8101878A, Cited in: EP 08169036.
P. Heinrich Stahl et al, Handbook of Pharmaceutical Salts Properties, Selection, and Use, International Union of Pure and Applied Chemistry (IUPAC), pp. 265-327.
Sophie-Dorothée Clas et al., Differential Scanning Calorimetry: Applications in Drug Development, vol. 2, No. 8, Aug. 1999, pp. 311-320.
Anonymous, The Complete Blog for the Preparation of Pharmaceutical Salts, Feb. 11, 2018, 10 pages.
International Search Report dated Dec. 12, 2010.

* cited by examiner

*Primary Examiner* — Shawquia Young
(74) *Attorney, Agent, or Firm* — Arent Fox LLP

(57) ABSTRACT

Pharmaceutically acceptable salts of sunitinib, processes of making sunitinib salts, as well as related pharmaceuticals and methods of treating are described.

7 Claims, 4 Drawing Sheets

SALTS OF SUNITINIB

CROSS-REFERENCE TO RELATED APPLICATION

This is a 371 National Stage entry of International Application No. PCT/EP2009/064215, filed 28 Oct. 2009, now WO 2010/049449A2 published 06 May 2010, which claims benefit of priority to European Patent Application No. 08167701.5 filed 28 Oct. 2008, the entire contents of which are incorporated herewith in their entirety by reference.

FIELD OF THE INVENTION

The present invention relates to novel pharmaceutically acceptable salts of sunitinib, to processes for their preparation and to pharmaceutical compositions containing them.

BACKGROUND OF THE INVENTION

The compound N-[2-(diethylamino)ethyl]-5-[-(5-fluoro-1,2-dihydro-2-oxo-3H-indol-3-ylidine)methyl]-2,4-dimethyl-1H-pyrrole-3-carboxamid, also named sunitinib (Formula I) has been shown to act as an inhibitor of protein kinases.

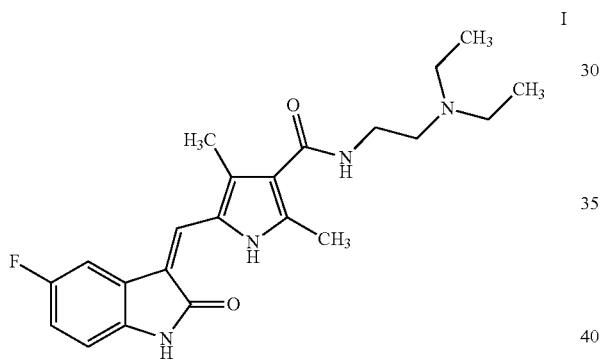

WO 01/60814 generally relates to pyrrole substituted 2-indolinone protein kinase inhibitors. Examples of salts for the general class of compounds are generally referred to, such as positively charged moieties including quaternary ammonium, salts such as the hydrochloride, sulfate, carbonate, lactate, tartrate, malate, maleate, succinate; and negatively charged species. WO 01/60814 is silent as to the preparation of and the nature of specific crystal forms of salts.

In WO 03/016305 it is said that the free base and salts of sunitinib (e.g. cyclamic acid, maleic acid, hydrobromic acid, mandelic acid, tartaric acid, fumaric acid, ascorbic acid, phosphoric acid, hydrochloric acid, p-toluenesulfonic acid, citric acid, and malic acid salts) had been screened for properties related to the processing of the salt and the preparation of oral pharmaceutical compositions therefrom, including, for example, crystallinity, toxicity, hygroscopicity, stability, and morphology, but only malate salt was chosen from the screening and only two crystal forms of sunitinib L-malate were specifically disclosed.

Salts often improve physical and biological characteristics of mother compounds without modifying primary pharmacological activity, based on mechanism of action.

Thus there is a continuing need to obtain new salts of sunitinib having improved physical and/or chemical properties. The present invention satisfies this need by providing new salts of sunitinib with a markedly enhanced solubility in water or aqueous media as an essential property of active pharmaceutical ingredients determining the performance of pharmaceutical formulation.

SUMMARY OF THE INVENTION

The present invention provides the following items including main aspects and preferred embodiments, which respectively alone and in combination particularly contribute to solving the above object and eventually provide additional advantages:

(1) Sunitinib salt with a pharmaceutically acceptable acid, the pharmaceutically acceptable acid being selected from the group consisting of D-tartaric acid, L-tartaric acid and citric acid, and hydrates and solvates of said salt.

(2) Sunitinib salt according to item (1), which is sunitinib D-tartrate, or a hydrate or solvate thereof, optionally being in crystalline form or in amorphous form.

(3) Sunitinib D-tartrate according to item (2) wherein said crystalline form is selected from the group consisting of:

a) Form I, characterized by XRD pattern having any 6 peaks at 2θ values selected from the group consisting of: 8.2, 10.5, 11.0, 13.0, 15.9, 16.5, 20.6 and 25.6, respectively exactly or ±0.2 degrees 2θ at the indicated 2θ values and/or by having a melting point falling in a range of 202-207° C.

b) Form II, characterized by XRD pattern having any 6 peaks at 2θ values selected from the group consisting of: 3.0, 3.3, 6.6, 8.2, 11.9, 14.2, 26.8, 27.9, respectively exactly or ±0.2 degrees 2θ at the indicated 2θ values and/or by having a melting point falling in a range of 183 to 193° C.

c) Form III, characterized by XRD pattern having any 6 peaks at 2θ values selected from the group consisting of: 5.7, 9.8, 13.4, 15.3, 16.5, 18.4, 22.2, 22.8, 26.5 and 28.4, respectively exactly or ±0.2 degrees 2θ at the indicated 2θ values and/or by having a melting point falling in a range of 219-226° C.

d) Form IV, characterized by XRD pattern having any 6 peaks at 2θ values selected from the group consisting of: 4.8, 12.2, 13.8, 19.3, 20.7, 22.7, 23.9, 25.6, 31.7 and 33.1, respectively exactly or ±0.2 degrees 2θ at the indicated 2θ values and/or by having a melting point falling in a range of 233-235° C., and combinations thereof.

(4) Sunitinib salt according to item (1), which is sunitinib L-tartrate, or a hydrate or solvate thereof, optionally being in crystalline form or in amorphous form.

(5) Sunitinib L-tartrate according to item (4) wherein said crystalline form is selected from the group consisting of:

a) Form I, characterized by XRD pattern having any 6 peaks at 2θ values selected from the group consisting of: 8.2, 10.5, 11.0, 13.0, 15.9, 16.5, 20.6 and 25.6, respectively exactly or ±0.2 degrees 2θ at the indicated 2θ values and/or by having a melting point falling in a range of 202-207° C.

b) Form II, characterized by XRD pattern having any 6 peaks at 2θ values selected from the group consisting of: 3.0, 3.3, 6.6, 8.2, 11.9, 14.2, 26.8, 27.9, respectively exactly or ±0.2 degrees 2θ at the indicated 2θ values and/or by having a melting point falling in a range of 183 to 193° C.

c) Form III, characterized by XRD pattern having any 6 peaks at 2θ values selected from the group consisting of: 5.7, 9.8, 13.4, 15.3, 16.5, 18.4, 22.2, 22.8, 26.5 and 28.4, respectively exactly or ±0.2 degrees 2θ at the indicated 2θ values and/or by having a melting point falling in a range of 219-226° C.

d) Form IV, characterized by XRD pattern having any 6 peaks at 2θ values selected from the group consisting of: 4.8, 12.2, 13.8, 19.3, 20.7, 22.7, 23.9, 25.6, 31.7 and 33.1, respectively exactly or ±0.2 degrees 2θ at the indicated 2θ values and/or by having a melting point falling in a range of 233-235° C., and combinations thereof.

(6) Sunitinib salt according to item (1), which is sunitinib citrate, or a hydrate or solvate thereof, optionally being in crystalline form or in amorphous form.

(7) Sunitinib citrate according to item (6)) wherein said crystalline form is selected from the group consisting of:

a) Form I, characterized by having a melting point falling in a range of 166-174° C.

b) Form II, characterized by having a melting point falling in a range of 185 to 198° C.

c) Form III, characterized by having a melting point falling in a range of 215-224° C.

and combinations thereof.

(8) Process for the preparation of a sunitinib salt according to any one of items (1) to (7) comprising the following steps:

providing a mixture comprising sunitinib (base) and an organic acid selected from the group consisting of D-tartaric, L-tartaric and citric acid;

isolating the obtained sunitinib salt.

(9) The process according to item (8), wherein said mixture is provided such that, after the sunitinib base and the selected organic acid have been dissolved in a liquid medium, the solution is maintained, optionally with agitating, at a temperature lower than 40° C., preferably than 30° C., until said sunitinib salt is formed; whereupon the obtained sunitinib salt is isolated from the liquid medium without increase of temperature to 40° C. or more.

(10) The process according to item (8) or (9), wherein said mixture is provided in methanol as solvent, and after dissolution is kept until salt formation at a temperature of about 20 to 25° C.

(11) A process for the preparation of sunitinib salt selected from the group consisting of sunitinib L-tartarate, sunitinib D-tartarate and sunitinib citrate, the process comprising the steps of:

a) mixing a compound of formula I, N-(2-(diethylamino)ethyl)-5-formyl-2,4-dimethyl-1H-pyrrole-3-carboxamide

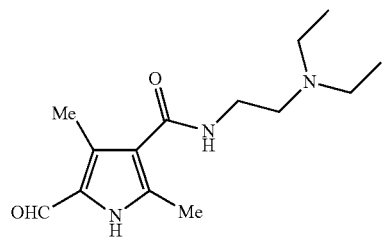

with compound of formula II, 5-fluoroindolin-2-one

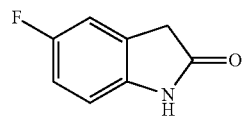

in a solvent;

b) refluxing the mixture obtained in step a);

c) adding acid selected from the group consisting of L-tartaric acid, D-tartaric acid and citric acid to a mixture subsequent to step b); and d) allowing the sunitinib salt selected from the group consisting of sunitinib L-tartarate, sunitinib D-tartarate and sunitinib citrate to precipitate subsequent to step c).

(12) The process according to item (11), wherein steps a) to d) are carried out in one pot without intermediate isolation of sunitinib base formed by steps a) and b).

(13) The process according to any one of items (11) to (12), wherein step a) is carried out in an organic solvent in the presence of organic base.

(14) The process according to item (13), wherein said organic solvent is lower alcohol, preferably ethanol.

(15) A pharmaceutical composition comprising a sunitinib salt according to any one of items (1) to (7).

(16) A pharmaceutical composition according to item (15), wherein said sunitinib salt is sunitinib D-tartrate.

(17) A pharmaceutical composition according to item (15), wherein said sunitinib salt is sunitinib L-tartrate.

(18) A pharmaceutical composition according to item (15), wherein said sunitinib salt is sunitinib citrate.

(19) Process for the preparation of a pharmaceutical composition comprising a sunitinib salt according to any one of items (1) to (7), wherein all steps involving processing of the sunitinib salt to obtain the desired final pharmaceutical composition is performed at a temperature lower than 40° C., preferably lower than 30° C.

(20) A pharmaceutical composition according to any one of items (15) to (18), or as prepared according to item (19) for use in the prophylaxis or therapeutic treatment of a protein kinase related disorder in an organism, preferably wherein said protein kinase related disorder is a cancer selected from squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

We have surprisingly found that using pharmaceutically acceptable ions selected from the group of D-tartaric, L-tartaric and citric acid, well defined salts of sunitinib with specific physico-chemical properties are formed.

Salts according to present invention (sunitinib citrate, sunitinib L-tartarate and sunitinib D-tartarate) are stable and show very good solubility in water. Based on the results found with the present invention, it is believed that the presence of at least two carboxylic acid groups, plus at least one hydroxyl group in the salts disclosed herein can be attributed to a markedly enhanced dissolution rate in water and aqueous solutions, thereby leading to an important improvement of sunitinib salts.

DETAILED DESCRIPTION OF THE INVENTION

In the following, the present invention will be described in more detail by preferred embodiments and examples while referring to the attached drawings, noting, however, that these embodiments, examples and drawings are presented for illustrative purposes only and shall not limit the invention in any way.

Figure 1:
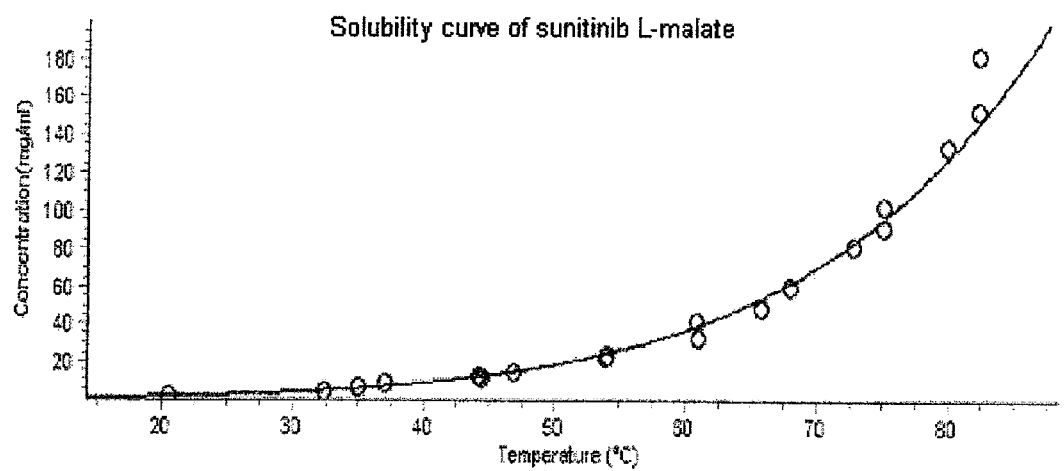
FIG. 1 shows solubility curve for sunitinib L-malate in water.
Figure 2:
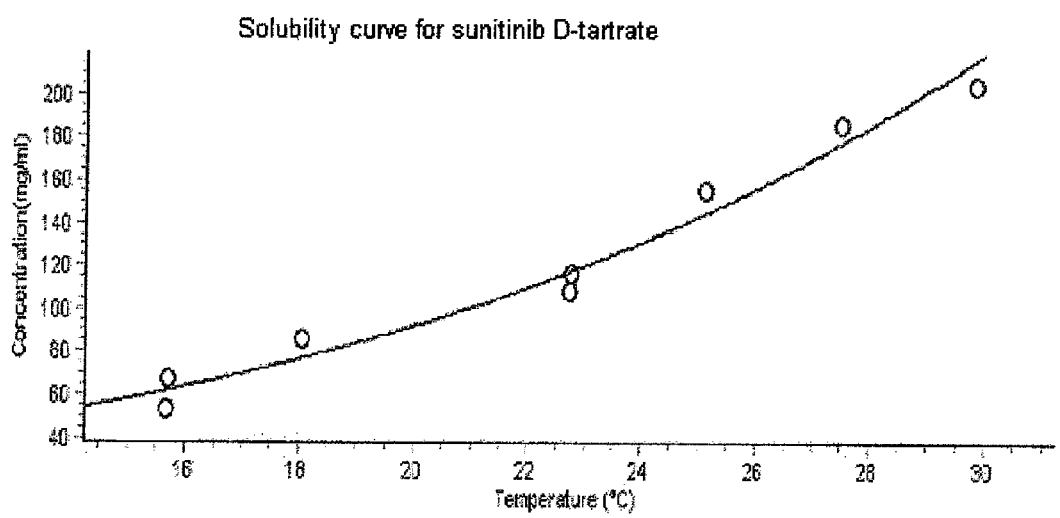
FIG. 2 shows solubility curve for sunitinib D-tartrate in water.
Figure 3:
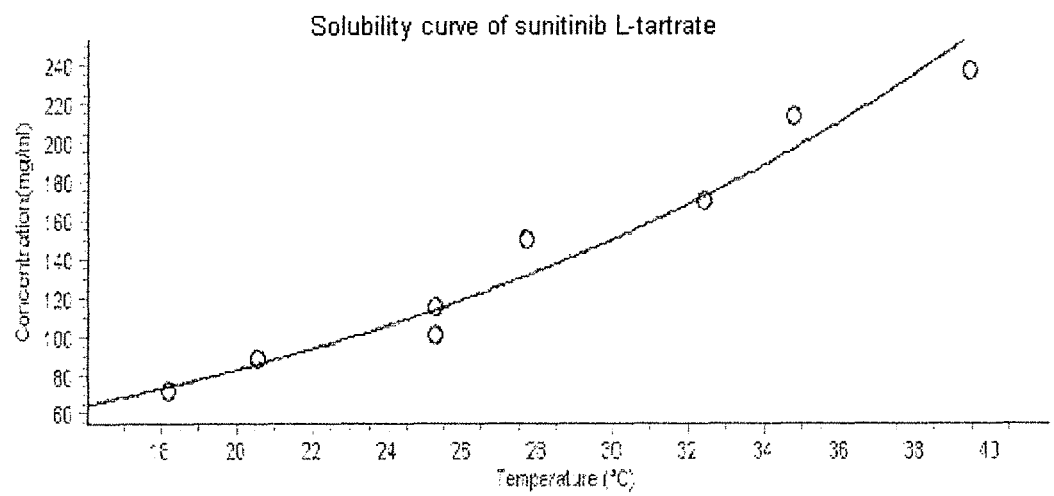
FIG. 3 shows solubility curve for sunitinib L-tartrate in water.
Figure 4:
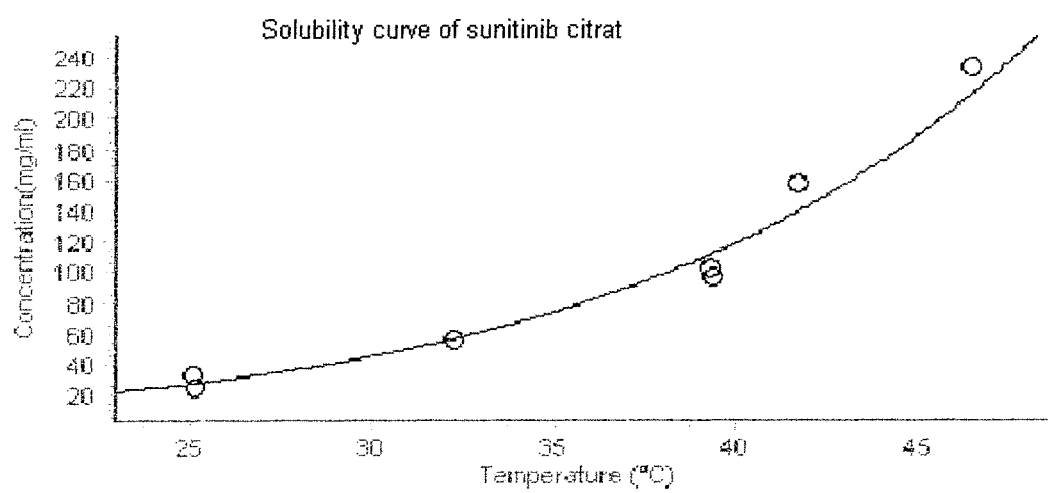
FIG. 4 shows solubility curve for sunitinib citrate in water.
Figure 5:
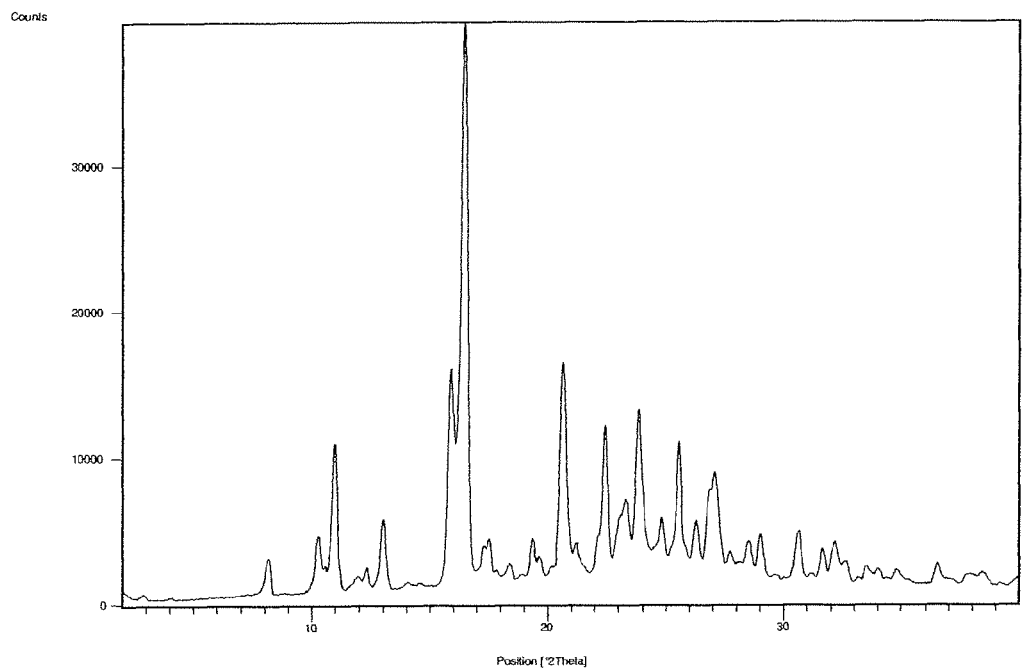
Figure 6:
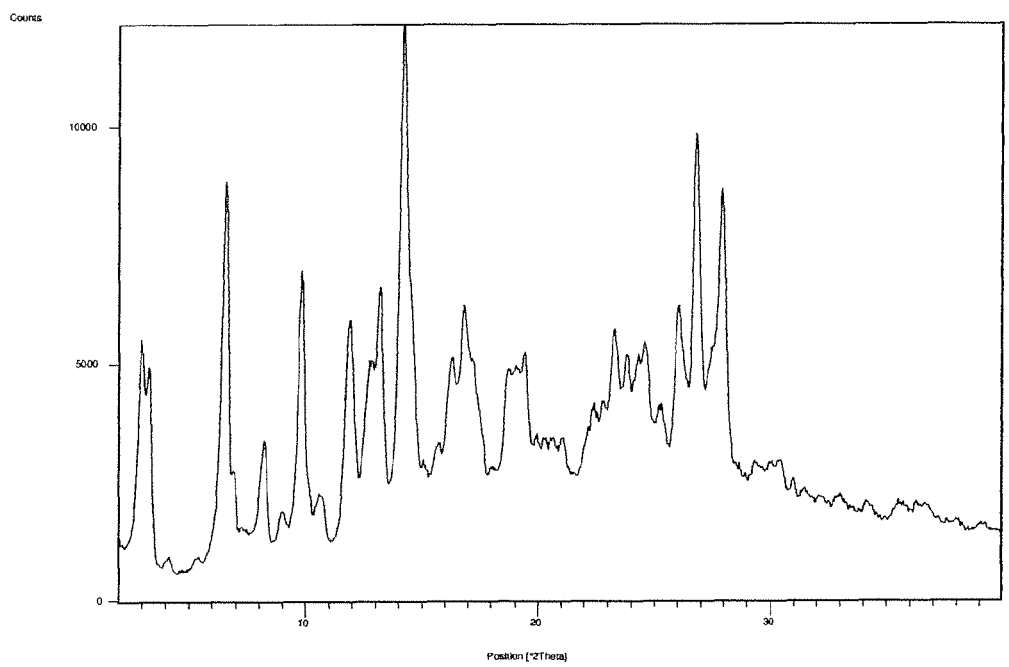
Figure 7:
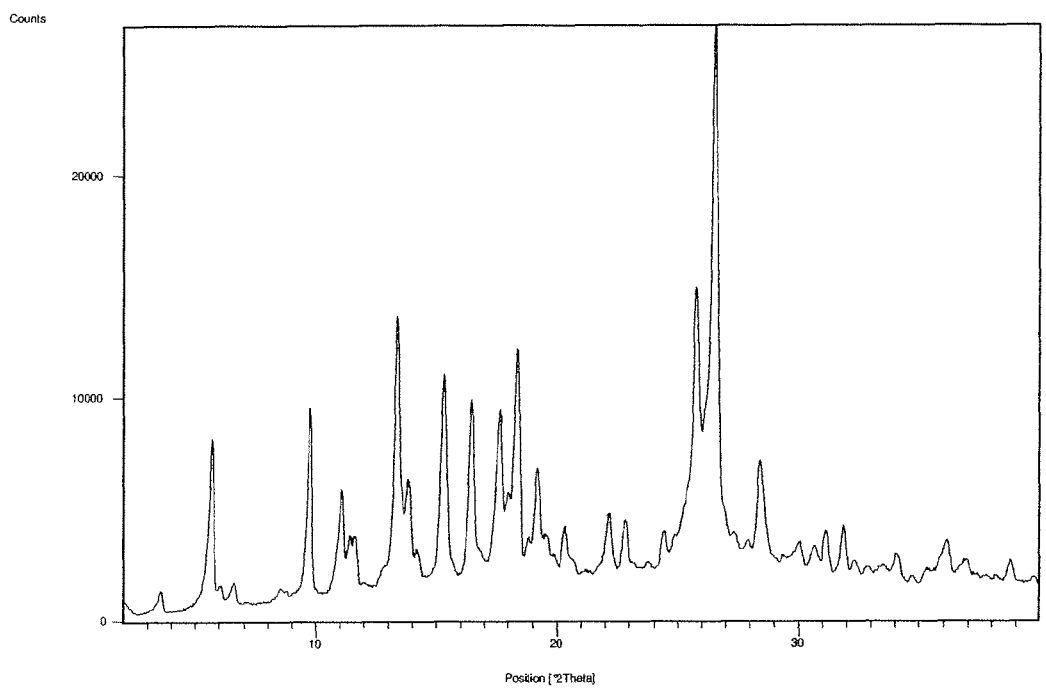
Figure 8:
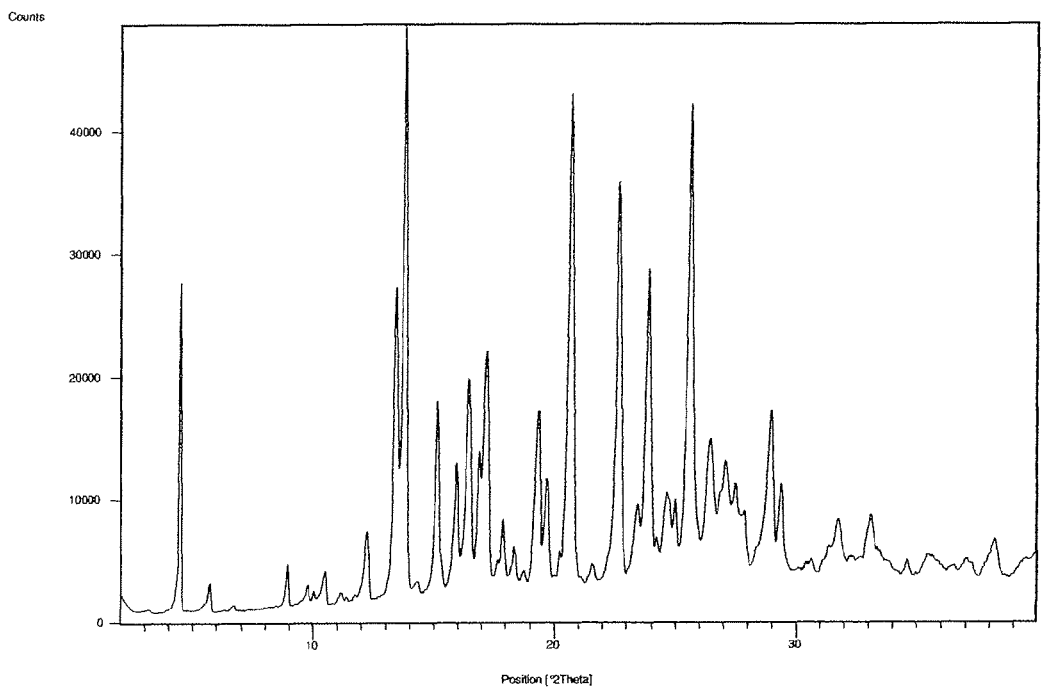

FIG. 5 shows characteristic X-Ray diffraction pattern of crystalline Form I of sunitinib D-tartrate or sunitinib L-tartrate of present invention FIG. 6 shows characteristic X-Ray diffraction pattern of crystalline Form II of sunitinib D-tartrate or sunitinib L-tartrate of present invention FIG. 7 shows characteristic X-Ray diffraction pattern of crystalline Form III of sunitinib D-tartrate or sunitinib L-tartrate of present invention FIG. 8 shows characteristic X-Ray diffraction pattern of crystalline crystalline Form IV of sunitinib D-tartrate or sunitinib L-tartrate of present invention In one aspect the present invention relates to novel salts of sunitinib selected from the group of consisting of D-tartaric, L-tartaric and citric acid.

In one aspect the present invention relates to hydrates and solvates of salts of sunitinib selected from the group of consisting of D-tartaric, L-tartaric and citric acid.

In another aspect the present invention relates to sunitinib D-tartrate or hydrate or solvate thereof.

In another aspect the present invention relates to crystalline sunitinib D-tartrate.

In another aspect the present invention relates to sunitinib D-tartrate in amorphous form.

In another aspect the present invention relates to sunitinib L-tartrate or hydrate or solvate thereof.

In another aspect the present invention relates to crystalline sunitinib L-tartrate.

In another aspect the present invention relates to sunitinib L-tartrate in amorphous form.

In another aspect the present invention relates to sunitinib citrate or hydrate or solvate thereof.

In another aspect the present invention relates to crystalline sunitinib citrate.

In another aspect the present invention relates to sunitinib citrate in amorphous form.

In another aspect the present invention relates to a process of preparing salts of sunitinib with pharmaceutically acceptable acids selected from the group of D-tartaric, L-tartaric and citric acid by providing a mixture of sunitinib base and pharmaceutically acceptable acid selected from the group of D-tartaric, L-tartaric and citric acid respectively in a suitable solvent system, comprised of a single solvent or a mixture of solvents, and isolating the obtained sunitinib salt by precipitation, filtration of the solid salt, evaporation, spray drying or other conventional techniques known in the art.

Suitable solvents are solvents selected from alcohols, ketones, nitriles, and esters or mixtures thereof, preferably selected from acetone, $C_1$-$C_4$ alcohols, acetonitrile, ethyl acetate. Most preferably methanol is used.

Pharmaceutically acceptable acid in natural state or in solution can be added to the solution of sunitinib base.

Pharmaceutically acceptable acid is preferably added in an equimolar ratio to sunitinib base or an excess of the acid is used.

The temperature of solvent system comprising a mixture of sunitinib base and pharmaceutically acceptable acid is from ambient temperature to the boiling point of the solvent system. After the sunitinib base and the selected organic acid have been dissolved in a liquid medium, the obtained solution is preferably kept at a temperature below 40° C., more preferably below 30° C., suitably at around ambient temperature such as about 20 to 25° C., until the salt is formed. Suitable time to form the salt is at least 2 hours, preferably at least 4 hours. Paying attention to such low temperature conditions contributes to obtain and maintain a stable salt form without otherwise risking the generation of decomposition products. It has been found that considerable amounts of decomposition or disintegration products appear with the salts of the present invention in solution at higher temperatures. Product characteristics such as melting point can be taken as a measure of stable salt form of the present invention.

Sunitinib salt can be isolated or recovered from the reaction solution by precipitation. The precipitation can be spontaneous depending on solvent system. Alternatively, the precipitation can be induced by reducing the temperature of reaction mixture, especially if initial temperature of reaction mixture is elevated. The precipitation can also be induced by reduction of solution volume, preferably under diminished pressure, or by complete evaporation of solvent. Furthermore, the precipitation may be caused by adding an antisolvent, e.g. water, ethers and hydrocarbons.

In one aspect of the invention sunitinib salt is prepared by adding pharmaceutically acceptable acid in natural state or in solution to the solution of sunitinib in a solvent of medium polarity, selected from alcohols, ketones, nitriles, and esters or mixtures thereof, preferably selected from acetone, $C_1$-$C_4$ alcohols, acetonitrile and ethyl acetate, optionally heating the mixture to obtain a solution and cooling. The precipitation of salt occurs after long standing the solution at appropriate temperature below 50° C., preferably between −10 to 25° C., after cooling the stirred mixture from heated solution below 50° C., preferably to room temperature or below, both after optional concentration of the solution by partial evaporation of solvents.

In another option the salt is formed by reprecipitation in a suspension of one or both starting components, or by precipitation adding antisolvent preferably selected from water, ethers and hydrocarbons, most preferably from water and diethyl ether.

In another aspect of the invention sunitinib salts are prepared by adding pharmaceutically acceptable acid in natural state or dissolved to a solution of sunitinib base in lower alcohol preferably methanol following by complete or partial evaporation of the solvents.

In another aspect of the present invention sunitinib D-tartrate, sunitinib L-tartrate or sunitinib citrate is prepared by adding D-tartaric acid, L-tartaric acid or citric acid, respectively in solid state to the solution of sunitinib in a solvent of medium polarity, selected from alcohols, ketones, nitriles, and esters, preferably selected from acetone, $C_1$-$C_4$ alcohols, acetonitrile and ethyl acetate, optionally heating the mixture to obtain a solution and cooling. The precipitation of salt occurs after long standing the solution at appropriate below 50° C., preferably between −20 to 25° C., after cooling the stirred mixture from heated solution below 50° C., preferably to room temperature or below, both after optional concentration of the solution by partial evaporation of solvents. In another option the salt is formed by reprecipitation in a suspension of one or both starting components, or by precipitation adding antisolvent preferably selected from water, ethers and hydrocarbons.

In another aspect of the present invention sunitinib D-tartrate, sunitinib L-tartrate or sunitinib citrate is prepared by adding D-tartaric acid, L-tartaric acid or citric acid, respectively in a solid state to a solution of sunitinib base in lower alcohol preferably methanol following by complete or partial evaporation of the solvents.

In one preferred example sunitinib base is dissolved in methanol. D-tartaric acid in a solid state is added to the solution of sunitinib base. The solution is preferably kept at a temperature lower than 40° C., preferably lower than 30° C. and typically at around room temperature such as about 20 to 25° C. The obtained precipitate is filtered.

Sunitinib D-tartrate prepared according to such procedure exhibits melting point at about 183 to 193° C., preferably at about 183 to 187° C., and might be further characterized by a powder X-ray diffraction pattern comprising the following characteristic reflection angles 2θ: 3.0±0.2°, 3.3±0.2°, 6.6±0.2°, 8.2±0.2°, 11.9±0.2°, 14.2±0.2°, 26.8±0.2° and 27.9±0.2° (Form II).

In another preferred example sunitinib base is dissolved in methanol. L-tartaric acid in a solid state is added to the solution of sunitinib base. The solution is preferably kept at a temperature lower than 40° C., preferably lower than 30° C. and typically at around room temperature such as about 20 to 25° C. The obtained precipitate is filtered.

Sunitinib L-tartrate prepared according to such procedure exhibits melting point at about 183 to 193° C., preferably at about 189 to 193° C., and might be further characterized by a powder X-ray diffraction pattern comprising the following characteristic reflection angles 2θ: 3.0±0.2°, 3.3±0.2°, 6.6±0.2°, 8.2±0.2°, 11.9±0.2°, 14.2±0.2°, 26.8±0.2° and 27.9±0.2° (Form II).

In another example boiling solutions of sunitinib base in ethanol and molar equivalent of L-tartaric acid in ethanol are combined, then kept at a temperature lower than 40° C., preferably lower than 30° C. and typically at around room temperature such as about 20 to 25° C. The obtained precipitate is filtered.

Sunitinib L-tartarate prepared according to such procedure exhibits melting point at about 202 to 207° C. and might be further characterized by a powder X-ray diffraction pattern comprising the following characteristic reflection angles 2θ: 8.2±0.2°, 10.5±0.2°, 11.0±0.2°, 13.0±0.2°, 15.9±0.2°, 16.5±0.2°, 20.6±0.2° and 25.6±0.2° (Form I).

In yet another example boiling solutions of sunitinib base in ethanol and molar equivalent of D-tartaric acid in ethanol are combined, then kept at a temperature lower than 40° C., preferably lower than 30° C. and typically at around room temperature such as about 20 to 25° C. The obtained precipitate is filtered.

Sunitinib D-tartarate prepared according to such procedure exhibits melting point at about 202 to 207° C. and might be further characterized by a powder X-ray diffraction pattern comprising the following characteristic reflection angles 2θ: 8.2±0.2°, 10.5±0.2°, 11.0±0.2°, 13.0±0.2°, 15.9±0.2°, 16.5±0.2°, 20.6±0.2° and 25.6±0.2°. (Form I)

In another example boiling solutions of sunitinib base in ethanol and about ½ of molar equivalent of L-tartaric acid in ethanol are combined, then kept at a temperature lower than 40° C., preferably lower than 30° C. and typically at around room temperature such as about 20 to 25° C. The obtained precipitate is filtered.

Sunitinib L-tartarate prepared according to such procedure exhibits melting point at about 233 to 235° C. and might be further characterized by a powder X-ray diffraction pattern comprising the following characteristic reflection angles 2θ: 4.8±0.2°, 12.2±0.2°, 13.8±0.2°, 19.3±0.2°, 20.7±0.2°, 22.7±0.2°, 23.9±0.2°, 25.6±0.2°, 31.7±0.2° and 33.1±0.2° (Form IV).

In yet another example boiling solutions of sunitinib base in ethanol and about ½ of molar equivalent of D-tartaric acid in ethanol are combined, then kept at a temperature lower than 40° C., preferably lower than 30° C. and typically at around room temperature such as about 20 to 25° C. The obtained precipitate is filtered.

Sunitinib D-tartarate prepared according to such procedure exhibits melting point at about 233 to 235° C. and might be further characterized by a powder X-ray diffraction pattern comprising the following characteristic reflection angles 2θ: 4.8±0.2°, 12.2±0.2°, 13.8±0.2°, 19.3±0.2°, 20.7±0.2°, 22.7±0.2°, 23.9±0.2°, 25.6±0.2°, 31.7±0.2° and 33.1±0.2° (Form IV).

In another example sunitinib base is dissolved in methanol. Citric acid in a solid state is added to the solution of sunitinib base. The solution is preferably kept at a temperature lower than 40° C., preferably lower than 30° C. and typically at around room temperature such as about 20 to 25° C. The obtained precipitate is filtered.

Sunitinib citrate prepared according to such procedure exhibits melting point at about 166 to 174° C. (Form I).

In another example sunitinib base and molar equivalent of citric acid are dissolved, while heating, in the mixture of methanol and water, preferably in 1:1 volumetric ratio. The solution is subsequently left to cool to about room temperature such as about 20 to 25° C. to give sunitinib citrate.

Sunitinib citrate prepared according to such procedure exhibits melting point at about 166-174° C. (Form I)

In yet another example sunitinib base dissolved in ethanol and about molar equivalent or slight excess of citric acid dissolved in ethanol are combined while heating, and left to cool to about room temperature such as about 20 to 25° C. to give sunitinib citrate.

Sunitinib citrate prepared according to such procedure exhibits melting points at about 166-174° C. (Form I), 185-198° C. (Form II) and 215-224° C. (Form III).

In yet another example sunitinib base is dissolved in boiling ethanol, subsequently citric acid is added to the solution, which is then left to cool to about room temperature such as about 20 to 25° C. to give sunitinib citrate.

Sunitinib citrate prepared according to such procedure exhibits melting points at about 166-174° C. (Form I) and 215-224° C. (Form III).

Another aspect of the present invention relates to a process for the preparation of sunitinib salt, preferably selected from the group consisting of sunitinib L-tartarate, sunitinib D-tartarate and sunitinib citrate comprising the following steps:
a) mixing a compound of formula I, N-(2-(diethylamino) ethyl)-5-formyl-2,4-dimethyl-1H-pyrrole-3-carboxamide

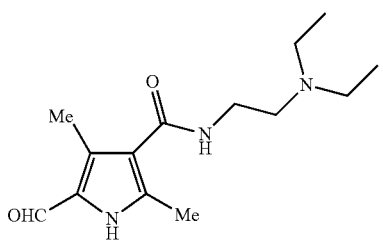

I with compound of formula II, 5-fluoroindolin-2-one

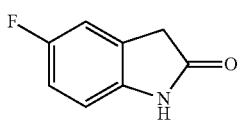

II in a solvent
b) refluxing the mixture obtained in step a);
c) adding acid, preferably selected from the group consisting of L-tartaric acid, D-tartaric acid and citric acid to a mixture subsequent to step b); and
d) allowing the sunitinib salt, preferably selected from the group consisting of sunitinib L-tartarate, sunitinib D-tartarate and sunitinib citrate to precipitate subsequent to step c).

This aspect of the present invention provides particularly efficient combination of process steps to repeatedly arrive at pure and physically stable sunitinib salt selected from the group consisting of sunitinib L-tartarate, sunitinib D-tartarate and sunitinib citrate. Formation of sunitinib and formation of its L-tartarate, D-tartarate or citrate salt according to this aspect of the present invention constitute parts of a common process, i.e. involving consecutive steps which start from relevant educts and finally yield the desired salt of sunitinib. The process is economically advantageous and allows the desired salt to be easily and repeatedly purified. It can be beneficially performable in one-pot, without intermediate isolation of sunitinib base formed by steps a) and b) being necessary.

Surprisingly, it has been found that the process according to the afore-defined aspect of the present invention allows to keep both the sunitinib base formed from steps a) and b) and the L-tartaric, D-tartaric or citric salt of sunitinib formed from step c) respectively in solution until step d) is started, for example by cooling the mixture obtained in step c). Maintaining the sunitinib base produced in partial step a) in solution, which is assisted by suitable means, including but not limited to e.g. choosing an appropriate solvent, adjusting an appropriate sunitinib compound concentration in solution, keeping the mixture at the boiling point of the liquid medium put under reflux, and adding L-tartaric acid, D-tartaric acid or citric acid to this mixture preferably at an elevated temperature and more preferably at the boiling point of the liquid medium but suitably still at a lower temperature down to room temperature, has been found significant to yield, in the step d), sunitinib salt selected from the group consisting of sunitinib L-tartarate, sunitinib D-tartarate and sunitinib citrate in stable and pure form.

Compound of formula I is mixed with and reacted with the compound of formula II in suitable solvent, preferably in an organic solvent and more preferably in the presence of organic base to form sunitinib. Organic solvent is preferably selected form the group consisting of alcohol, acetonitrile, dialkyl ketone, acetonitrile, formamide and mixtures thereof. Most preferably organic solvent is ethanol. Its relatively high boiling point is advantageous for the reaction to take place rapidly, and in combination therewith it provides for dissolution of sunitinib.

The desired concentration is preferably about 15-25 mg/ml of hypothetically formed sunitinib in order to prevent the precipitation of sunitinib out of solution in this stage of process, i.e. before sunitinib salt is formed or the formed salt is precipitated or crystallized in a premature state. Appropriate conditions can be chosen to adjust such beneficial concentration of sunitinib base formed, including but not limited to using correspondingly calculated amounts of educts for the reaction step a), volume of the reaction medium, and the like.

Suitable organic base is selected form the group consisting of linear amines, such as for example monoalkyl, dialkyl and trialkyl amines, cyclic amines, such as for example pyrrolidine, and alkoxides. Most preferably organic base is pyrrolidine.

A molar ratio of compound of formula I to compound II is preferably about 1:1.

The reaction mixture is refluxed, preferably for about 0.5-10 hours, more preferably about 5 hours. Subsequently acid selected from the group consisting of sunitinib L-tartarate, sunitinib D-tartarate and sunitinib citrate is added, preferably in the ratio of about 1:2 or in about the equimolar ratio to compounds of formula I and II.

Sunitinib salt can be isolated or recovered from the reaction solution by precipitation, while optionally allowing the desired crystal form to crystallize. The precipitation can be spontaneous depending on solvent system. Alternatively, the precipitation can be induced by reducing the temperature of reaction mixture, especially if initial temperature of reaction mixture is elevated. The precipitation can also be induced by reduction of solution volume, preferably under diminished pressure, or by complete evaporation of solvent. Furthermore, the precipitation may be caused by adding an antisolvent, e.g. water, ethers and hydrocarbons.

In one aspect of the invention the precipitation sunitinib salt occurs after long standing the solution at appropriate temperature below 50° C., preferably between −10 to 30° C., most preferably at room temperature at about 20 to 25° C., while optionally stirring, after cooling optionally stirred mixture from heated solution below 50° C., preferably to room temperature or below, both after optional concentration of the solution by partial evaporation of solvents.

In another option sunitinib slat is formed by precipitation adding antisolvent preferably selected from water, ethers and hydrocarbons.

Obtained sunitinib salt may be separated by techniques well known in the art, e.g. filtration, centrifugation, decanting. Preferably filtration is used.

Sunitinib L-tartarate prepared according to such procedure exhibits melting point at about 219 to 226° C. and might be further characterized by a powder X-ray diffraction pattern comprising the following characteristic reflection angles 2θ: 5.7±0.2°, 9.8±0.2°, 13.4±0.2°, 15.3±0.2°, 16.5±0.2°, 18.4±0.2°, 22.2±0.2°, 22.8±0.2°, 26.5±0.2° and 28.4±0.2° (Form III).

Sunitinib D-tartarate prepared according to such procedure exhibits melting point at about 219 to 226° C. and might be further characterized by a powder X-ray diffraction pattern comprising the following characteristic reflection angles 2θ:

5.7±0.2°, 9.8±0.2°, 13.4±0.2°, 15.3±0.2°, 16.5±0.2°, 18.4±0.2°, 22.2±0.2°, 22.8±0.2°, 26.5±0.2° and 28.4±0.2° (Form III).

Another aspect of the present invention is a pharmaceutical composition for administering a therapeutically effective amount of sunitinib salts with pharmaceutically acceptable acid of the present invention, preferably sunitinib D-tartrate, sunitinib L-tartrate or sunitinib citrate, in unit dosage form with one or more pharmaceutically acceptable carriers or other excipients.

A therapeutically effective amount of sunitinib salt of the present invention is amount of salt ranging, when calculated as sunitinib base, from 5 to 150 mg, preferably from 10 to 100 mg, more preferably from 10 to 50 mg.

Pharmaceutical acceptable salts in accordance with present invention can be embodied for example in form of tablet, capsules, pellets, granules and suppositories or their combined forms. Pharmaceutical composition in accordance with present invention can be suitable for immediate release or modified release of sunitinib salts of the present invention. Solid pharmaceutical compositions can be for example coated with aim of increasing peletibility or regulating the disintegration or absorption.

Pharmaceutically acceptable excipients may be selected from the group consisting of binders, diluents, disintegrating agents, stabilizing agents, preservatives, lubricants, fragrances, flavoring agents, sweeteners and other excipients known in the field of the pharmaceutical technology. Preferably, carriers and excipients may be selected from the group consisting of lactose, microcrystalline cellulose, cellulose derivatives, (e.g. hydroxypropylcellulose, croscarmellose sodium), polyacrylates, calcium carbonate, starch, colloidal silicone dioxide, sodium starch glycolate, talc, magnesium stearate, mannitol, polyvinylpyrrolidone, polyethylene glycol and other excipients known in the field of the pharmaceutical technology.

Optionally, the pharmaceutical compositions of the invention may be combination products comprising one or more additional pharmaceutically active components in addition to sunitinib salts.

The pharmaceutical compositions according to the present invention may be prepared by methods known in the field of the pharmaceutical technology. In view of the temperature sensitivity of the sunitinib salts disclosed herein, a preferred embodiment of the process for the preparation of a pharmaceutical composition according to the present invention however is one where all steps involving processing of the sunitinib salt to obtain the desired final pharmaceutical composition are performed at a temperature lower than 40° C., preferably than 30° C. This particularly applies to steps performed in solution or under wet conditions. As a result, the respective sunitinib salt can maintain stability and produce less decomposition products. Stability and production of less decomposition products can be defined by respective melting points disclosed herein.

The further aspect of the present invention is a method for treatment of a protein kinase related disorder in an organism, with a medicament by using an effective amount of sunitinib salts according to the present invention, preferably sunitinib D-tartrate, sunitinib L-tartrate or sunitinib citrate.

In another aspect the present invention is related to use of sunitinib salts according to present invention, preferably sunitinib D-tartrate, sunitinib L-tartrate or sunitinib citrate, for the manufacture of medicament for treatment of a protein kinase related disorder in an organism. Said protein kinase related disorder is preferably a cancer selected from squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

EXPERIMENTAL PROCEDURES

TABLE 1

Solubility of sunitinib salts in water at 25° C.

| 25° C. | L-malate | D-tartrate | L-tartrate | citrate |
|---|---|---|---|---|
| mg/ml (water) | 2 | 142 | 111 | 30 |

The solubility in water was measured using Crystal16 ™ from Avantium Technologies.

From the results shown in Table 1 and FIGS. 1 to 4, it can be seen that solubility in water at 25° C. is remarkably increased relative to L-malate salt when the sunitinib salt is selected from the group consisting of sunitinib D-tartrate, sunitinib L-tartrate or sunitinib citrate.

Sunitinib L-malate was prepared according to the procedure described in Example 1 in WO 03/016305.

Sunitinib free base may be prepared according to the general procedures of WO 01/60814.

General Procedure of the Examples:

Sunitinib base was suspended in suitable solvent, acid (1 molar equivalent) was added and the suspension was heated until all material dissolved. Solution was left to cool to room temperature. After a while, the appropriate salt was formed as a crystalline precipitate. Suspensions were heated or left at room temperature to dissolve. Salts crystallized from solution or were isolated by evaporation of solvent.

According to this general procedure, appropriate salts might be prepared using for example D-mandelic, hippuric, trans-cinnamic, D-tartaric, L-tartaric, malonic, citric, oxalic, glutaric, 1-hydroxy-2-naphtolic, benzoic, (−)-camphor-10-sulfonic, salicylic, crotonic, ascorbic and hydrochloric acid.

Apart from the methanol, 2-propanol, acetonitrile, water and mixtures thereof to prepare solutions/suspensions of sunitinib base and acid were used Example 1

Sunitinib (2.20, 5.52 mmol) was suspended in methanol (100 ml). 0.83 g of D-tartaric acid was added. Mixture was heated until all material was dissolved, then left to cool to room temperature to form crystalline sunitinib D-tartrate, 2.95 g. Melting point 183-187° C. (form II)

Example 2

Sunitinib (2.15, 5.40 mmol) was suspended in methanol (100 ml). 0.81 g of L-tartaric acid was added. Mixture was heated until all material was dissolved, then left to cool to room temperature to form crystalline sunitinib L-tartrate, 2.1 g. Melting point: 189-193° C. (form II)

Example 3

Sunitinib (2.21 g, 5.55 mmol) suspended in methanol (75 ml), 1.07 g of citric acid was added. Mixture was stirred at room temperature for several hours, and then filtered to obtain crystalline sunitinib citrate, 3.2 g. Melting point: 166-174° C. (Form I).

Example 4

Sunitinib (1.41 g, 3.53 mmol) was dissolved in boiling ethanol (130 ml), to which a solution of L-tartaric acid (0.53 g in 10 ml ethanol) was added and left to cool to room temperature to give 1.78 g of sunitinib L-tartarate. Melting point: 202-205° C. (Form I), ratio sunitinib/tartaric acid (according to NMR) 1:1.

Example 5

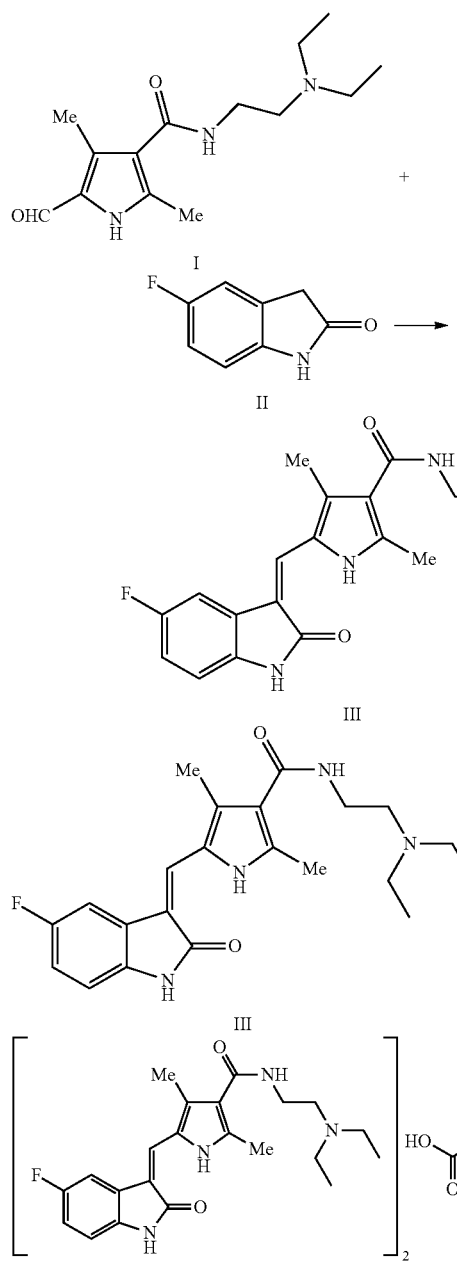

To a solution of 6.63 g (25 mmol) N-(2-(diethylamino)ethyl)-5-formyl-2,4-dimethyl-1H-pyrrole-3-carboxamide (I) and 3.78 g (25 mmol) 5-fluoroindolin-2-one (II) in ethanol (400 ml), 0.25 ml of pyrrolidine was added and mixture was refluxed for 5 h. To a boiling reaction mixture, a solution of L-tartaric acid (1.88 g, 12.5 mmol) in ethanol (20 ml) was added and solution was left to cool to room temperature, with slow (as slow as possible) stirring. The stirring was continued for another 16 hours, then the product was filtered to get 4.20 g of sunitinib L-tartarate. Melting point: 219-223° C. (Form III), ratio sunitinib/tartaric acid (according to NMR) 2:1.

Example 6

Sunitinib (1.35 g, 3.39 mmol) was dissolved in boiling ethanol (140 ml), to which a solution of L-tartaric acid (0.25 g in 10 ml ethanol) was added and left to cool to room temperature to give 1.78 g of sunitinib L-tartarate. Melting point: 233-235° C. (form IV), ratio sunitinib/tartaric acid (according to NMR) 2:1.

Example 7

Sunitinib (5.41 g, 13.6 mmol) was dissolved in boiling ethanol (540 ml), to which a solution of D-tartaric acid (2.24 g, 15 mmol) in ethanol (25 ml) was added and left to cool to room temperature to give 7.41 g of sunitinib D-tartarate. Melting point: 205-207° C. (Form I), ratio sunitinib/tartaric acid (according to NMR) 1:1.

Example 8

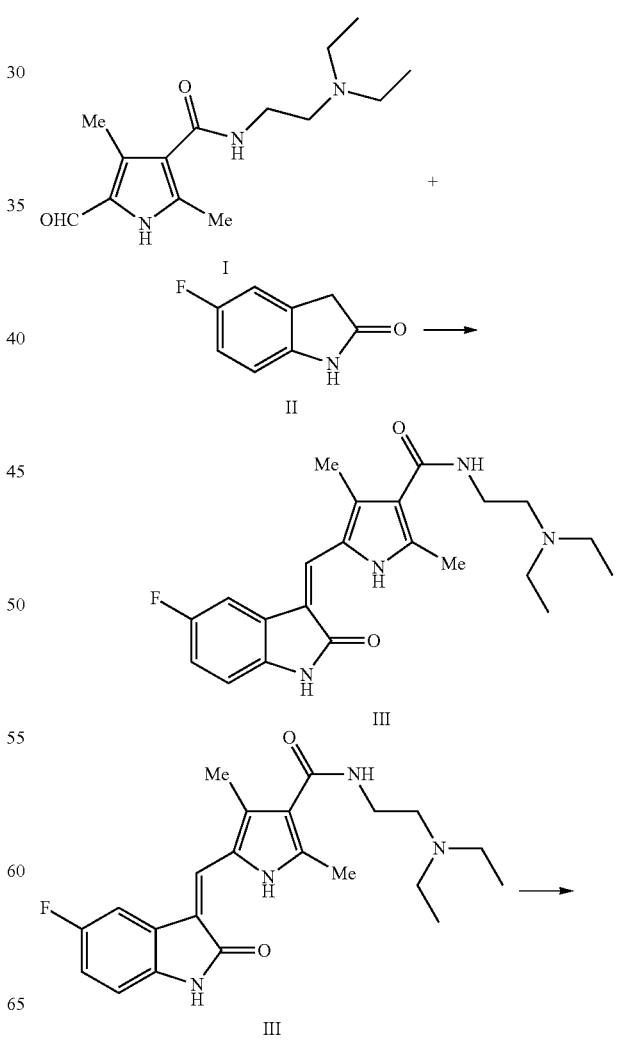

-continued

[Structure of sunitinib with tartaric acid, ratio 2:1]

To a solution of 6.63 g (25 mmol) N-(2-(diethylamino)ethyl)-5-formyl-2,4-dimethyl-1H-pyrrole-3-carboxamide (I) and 3.78 g (25 mmol) 5-fluoroindolin-2-one (II) in ethanol (400 ml), 0.25 ml of pyrrolidine was added and mixture was refluxed for 5 h. To a boiling reaction mixture, a solution of D-tartaric acid (1.88 g, 12.5 mmol) in ethanol (20 ml) was added and a solution was left to cool to room temperature, with slow (as slow as possible) stirring. The stirring was continued for another 16 hours, then the product was filtered to get 4.53 g of sunitinib D-tartarate. Melting point: 220-226° C. (Form III), ratio sunitinib/tartaric acid (according to NMR) 2:1.

Example 9

Sunitinib (7.42 g, 18.6 mmol) was dissolved in boiling ethanol (700 ml), to which a solution of D-tartaric acid (1.40 g) in ethanol (20 ml) was added and left to cool to room temperature to give 8.08 g of sunitinib D-tartarate: Melting point: 233-235° C. (Form IV), ratio sunitinib/tartaric acid (according to NMR) 2:1.

Example 10

Sunitinib (2.25 g, 5.65 mmol) and citric acid (1.09 g, 5.65 mmol) were dissolved while heating in the mixture of methanol (100 ml) and water (10 ml). The solution was left to cool to room temperature to give sunitinib citrate. Melting point: 168-173° C. (Form I).

Example 11

Sunitinib (1.19 g, 2.99 mmol) dissolved in ethanol (120 ml) and citric acid (0.63 g, 3.29 mmol) dissolved in ethanol (10 ml) were combined while heating, and left to cool to room temperature to give sunitinib citrate with melting points 167-173° C. (Form I), 185-198° C. (Form II) and 215-222° C. (Form III).

Example 12

Sunitinib (1.45 g, 3.64 mmol) was dissolved in boiling ethanol (140 ml), then citric acid (0.23 g, 1.21 mmol) was added to the solution, which was left to cool to room temperature to give sunitinib citrate with melting points 166-170° C. (Form I) and 219-224° C. (Form III).

Methods of Analysis

The products were analyzed by following methods:

X-Ray Powder Diffraction Method:

Conditions for obtaining powder X-ray diffraction (XRD) patterns: The powder X-ray diffraction patterns were obtained by methods known in the art using Philips X'Pert PRO diffractometer with X'Celerator detector using CuKα radiation (tube operating at 45 kV and 40 mA) in the Bragg-Brentano (reflection) geometry. Data were recorded from 2 to 40° 2θ in steps of 0.033° 2θ and the measurement time of 50 seconds per step. Variable divergence and antiscatter slits were used to maintain 12 mm of sample length irradiated.

Differential Scanning calorimetry:

Conditions for obtaining DSC thermograms: Thermograms were obtained with Mettler Toledo DSC822e differential scanning calorimeter. The sample (4-6 mg) was placed in an unsealed aluminium pan with a hole and heated at 5° C./min in the temperature range from 30° C. to 250° C.

The invention claimed is:

1. A pharmaceutically acceptable acidic salt of crystalline Form I of sunitinib with water solubility of 30 mg/ml or higher, wherein the acid with the salt is selected from the group consisting of D-tartaric acid and L-tartaric acid.

2. The sunitinib salt according to claim 1, which is sunitinib D-tartrate.

3. The sunitinib D-tartrate according to claim 2 wherein Form I is characterized by XRD pattern comprising 6 peaks at 2θ values selected from the group consisting of: 8.2, 10.5, 11.0, 13.0, 15.9, 16.5, 20.6 and 25.6, exactly or ±0.2 degrees 2θ at the indicated 2θ values and/or by having a melting point within the range of 202-207° C.

4. The sunitinib salt according to claim 1, which is sunitinib L-tartrate.

5. The sunitinib L-tartrate according to claim 4, wherein Form I is characterized by XRD pattern comprising 6 peaks at 2θ values selected from the group consisting of: 8.2, 10.5, 11.0, 13.0, 15.9, 16.5, 20.6 and 25.6, exactly or ±0.2 degrees 2θ at the indicated 2θ values and/or by having a melting point within the range of 202-207°.

6. A pharmaceutical composition comprising a sunitinib salt according to claim 1.

7. A method of treating a protein kinase related disorder in an organism, wherein said protein kinase related disorder is a cancer selected from the group consisting of glioblastoma, lung cancer, ovarian cancer, breast cancer, small-cell lung cancer, glioma and gastrointestinal cancer, comprising administering to a patient in need thereof, an effective amount of the pharmaceutical composition of claim 6.

* * * * *